United States Patent

Whitmore, III et al.

[11] Patent Number: 6,126,607
[45] Date of Patent: Oct. 3, 2000

[54] ULTRASOUND INTERFACE CONTROL SYSTEM

[75] Inventors: Willet F. Whitmore, III; Winston E. Barzell, both of Sarasota, Fla.

[73] Assignee: Barzell-Whitmore Maroon Bells, Inc., Sarasota, Fla.

[21] Appl. No.: 09/184,070

[22] Filed: Nov. 2, 1998

Related U.S. Application Data

[60] Provisional application No. 60/064,131, Nov. 3, 1997.

[51] Int. Cl.[7] .................................................... A61B 8/14
[52] U.S. Cl. .......................................................... 600/459
[58] Field of Search .................................. 600/459, 462, 600/463, 466, 470; 29/25–35; 604/19–22, 53, 96; 73/623; 606/213–18

[56] References Cited

U.S. PATENT DOCUMENTS

| | | | |
|---|---|---|---|
| 4,579,123 | 4/1986 | Chen et al. | 600/459 |
| 4,794,931 | 1/1989 | Yock | 128/660.03 |
| 4,815,470 | 3/1989 | Curtis et al. | 128/662.03 |
| 4,911,173 | 3/1990 | Terwilliger | 128/662.06 |
| 5,152,294 | 10/1992 | Mochizuki et al. | 600/459 |
| 5,190,046 | 3/1993 | Shturman | 128/662.06 |
| 5,199,437 | 4/1993 | Langberg | 128/662.06 |
| 5,201,706 | 4/1993 | Noguchi et al. | 604/96 |
| 5,265,612 | 11/1993 | Sarvazyan et al. | 128/660.01 |
| 5,331,947 | 7/1994 | Shturman | 600/463 |
| 5,335,663 | 8/1994 | Oakley et al. | 128/662 |
| 5,423,332 | 6/1995 | Zirps et al. | 128/774 |
| 5,438,997 | 8/1995 | Sieben et al. | 128/662.06 |
| 5,469,853 | 11/1995 | Law et al. | 600/462 |
| 5,603,327 | 2/1997 | Eberle et al. | 128/662.06 |
| 5,623,940 | 4/1997 | Daikuzono | 128/736 |
| 5,640,961 | 6/1997 | Verdonk | 128/662.06 |
| 5,671,747 | 9/1997 | Connor | 128/662.06 |
| 5,672,153 | 9/1997 | Lax et al. | 604/22 |
| 5,685,839 | 11/1997 | Edwards et al. | 604/22 |

FOREIGN PATENT DOCUMENTS 39 29 612 A1  5/1990  Germany .

*Primary Examiner*—Marvin M. Lateef
*Assistant Examiner*—Ali M. Imam
*Attorney, Agent, or Firm*—Pennie & Edmonds LLP

[57] ABSTRACT

A system for forming a liquid interface between a body tissue and an ultrasound probe which includes an ultrasound transducer. The system including a sheath including a liquid tight sack, wherein the sack covers, when the probe is placed inside the sheath, at least a portion of the probe where the ultrasound transducer is positioned but without covering an underside of the probe located on a diametrically opposite side from where the ultrasound transducer is positioned. The system also includes a tube connected to the sheath, wherein the sack expands to form the liquid interface when a liquid is introduced to the sack via the tube.

18 Claims, 3 Drawing Sheets

ULTRASOUND INTERFACE CONTROL SYSTEM

Cross-Reference to Related Applications

This application claims the benenfit of U.S. Provisional Application No. 60/064,131, filed Nov. 3, 1997.

FIELD OF THE INVENTION

The present invention is directed to a device for ultrasound imaging, and in particular to a device for controlling a fluid interface between an ultrasound imaging probe and body tissue being imaged.

BACKGROUND OF THE INVENTION

Ultrasound imaging is an increasingly valuable medical tool for both diagnosis and therapy of human disease. For example, transrectal ultrasound imaging is employed to image the prostate in the treatment of prostatic cancer. In this application, a specially designed ultrasound imaging probe is placed in the rectum transanally after the rectum has been evacuated of stool and gas. The tip of the probe contains one or more ultrasound transducers transmitting and receiving at selected ultrasonic frequencies to image body tissues.

Regardless of the specific application, the optimal ultrasound images are obtained when there is a suitable liquid or semi-liquid interface between the tissue being imaged and the ultrasound transducer. This interface provides clear transmission paths for ultrasound waves emanating from the ultrasound transducer to the tissue and waves reflecting back from the tissue to the ultrasound transducer. The interface also helps to position the ultrasound transducer at distances from the tissue being imaged which fall within the range of focal lengths of the ultrasound transducer.

Most ultrasound probe manufacturers have developed a watertight sheath or condom with which to cover the ultrasound transducer at the tip of the probe. As illustrated in FIG. 1, a conventional sheath 203 is filled with fluid to provide the required liquid interface. Typically, this sheath encasing at the end of an ultrasound probe 201 forms a circumferential, essentially spherical, and omni-directional liquid tight balloon cover which is filled to the desired volume with water or saline. The liquid volume added will, to some extent, determine the separation of the ultrasound transducer in the probe from the tissue to be imaged and displace extraneous gas or stool fragments in the rectum which may interfere with the ultrasonic waves emanating from the ultrasound transducer.

All existing systems employing the conventional interface have a major deficiency. That is, the thickness and position of the interface in relation to the ultrasound transducer becomes inconsistent in an unpredictable manner, because the balloon of liquid surrounding the tip of the probe is deflected in an uncontrolled and undesirable way by gravity and contours formed by surrounding tissues. Movement of the probe tip within this fluid sack is thus largely variable, difficult to control, and may result in inferior images. The effects of gravity and the surrounding tissues are particularly troublesome when performing procedures in the lithotomy position usually used in transrectal ultrasound imaging for prostate biopsies under anesthesia, brachytherapy, or laser ablation.

U.S. Pat. No. 5,265,612 discloses a sheath for an intracavity ultrasonic device having regions of different elasticity. An area of the sheath near the ultrasound transducer is of greater elasticity, which facilitates localized deformation of a selected region of the tissue. As shown in FIG. 1 of this patent, other areas of the sheath still can expand under the fluid pressure. Moreover, manufacture of the sheath is difficult and, is not cost effective, given that it is desirable to have single-use, disposable sheaths. U.S. Pat. No. 5,623,940 discloses a catheter with a balloon which is inflatable out from an inflation window in a covering which encases all of the catheter. The diameter of the entire catheter assembly is substantially increased. As a result, insertion and removal of the catheter becomes more difficult and painful if the patient is awake.

Thus, there exists a need for an improved device for controlling the interface between an ultrasound imaging probe and the tissue being imaged.

SUMMARY OF THE INVENTION

The present invention provides a system for forming a liquid interface between a body tissue and an ultrasound probe which includes an ultrasound transducer. The system comprises of a sheath configured and dimensioned to receive at least a portion of the probe, the sheath including a liquid tight expandable sack which covers the ultrasound transducer and a portion of the top side of the probe without covering the bottom side of the probe; and a tube operatively associated with the sack for directing a fluid into the sack for expansion thereof to form a liquid interface.

In one aspect of the invention, the system further comprises a patch affixed to the sheath, wherein the patch and the sheath form the liquid tight sack. In another embodiment, the sheath includes first and second layers affixed to each other to form the liquid tight sack.

In yet another embodiment, the system further comprises a fastener to secure the sheath to the probe and to form the liquid tight sack between the sheath and the probe; and a splint made of a rigid material configured to restrict the sheath from expanding from the bottom side of the probe. In this embodiment, the fastener includes at least one o-ring. Alternatively, the splint is a separate component that is positioned over a portion of the sheath and is fastened to the probe. In yet another embodiment, the splint is integrally formed with the sheath.

In another aspect of the invention, the area covered by the sack on the probe is substantially delineated in part by an intersection between an imaginary longitudinal plane and the surface of the probe, wherein the longitudinal plane is located between ⅖ and ⅘ of the radius of the probe from the top side of the probe.

In yet another aspect of the invention the sheath further comprises a fluid introduction port configured to be connected to the fluid introduction tube.

The invention also provides a system for covering an ultrasonic probe, the probe having top and bottom sides and including an ultrasound transducer on the top side thereof. The system comprises a sheath with a liquid tight sack which is configured and dimensioned to cover the ultrasound transducer and a portion of the top side of the probe when the probe is placed inside the sheath, without covering the bottom side of the probe; and a fluid introduction port configured to receive a tube for introducing liquid into the sack, wherein the sack expands when receiving liquid to form the liquid interface.

The system further comprises a patch affixed to the sheath, wherein the patch and the sheath form the liquid tight sack. In an alternative embodiment, the system further includes first and second layers affixed to each other to form the liquid tight sack.

In yet another alternative embodiment, the system further comprises a fastener to secure the sheath to the probe and to form the liquid tight sack between the sheath and the probe; and a splint made of a rigid material configured to restrict the sheath from expanding from the underside of the probe. In this embodiment, the fastener includes at least one o-ring. Alternatively, the splint is formed on the sheath. In addition, the splint is fastened to the probe.

In another aspect of the invention, the area covered by the sack on the probe is substantially delineated in part by an intersection between an imaginary longitudinal plane and the surface of the probe, wherein the longitudinal plane is located between from ⅖ and ⅘ of the radius of the probe from a surface of the probe where the ultrasound transducer is located.

The invention also provides a system for forming a liquid interface between body tissue and an ultrasound probe, the probe having top and bottom sides and including an ultrasound transducer on the top side thereof. The system comprises a sheath covering at least a portion of the ultrasonic probe and having a fluid introduction port for introducing fluid into the sheath to expand the sheath, an ultrasonic probe tip insertable into a body cavity, and at least one transducer located on the probe tip for imaging body tissue; and a splint. The splint comprises a body section configured and dimensioned to fit around a portion of the ultrasonic probe; a cradling section extending from the body section and substantially covering a region of the ultrasonic probe tip opposite the transducer; and at least one fastening element for securing the splint to the ultrasonic probe, wherein the splint is made of a material having sufficient rigidity to substantially prevent the sheath from expanding in the region covered by the cradling section.

DESCRIPTION OF THE PREFERRED EMBODIMENTS

Figure 2:
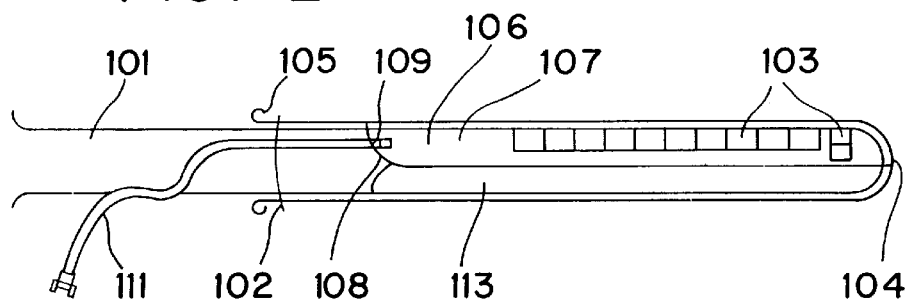
FIG. 2 is a side view of a probe with a sheath, which includes a sack, according to the first embodiment of the present invention.

Referring to FIG. 2, a first preferred embodiment of the present invention includes a probe 101, a sheath 105 designed to snugly fit over the probe 101, and a fluid introduction tube 111.

The probe 101 has a cylindrical body and includes one or more ultrasound transducers 103 which transmit and receive ultrasound waves for generating images of tissues. The diameter of the probe 101 is approximately 2 cm, and the probe length can be up to 10 cm. Different parts of the probe 101 are designated with appropriate names in order to accurately describe the present invention, as the following: a transducer region 107 includes a surface area of the probe 101 in which the ultrasound transducer 103 is positioned and which allows unobstructed paths for ultrasound waves emanating from the ultrasound transducer 103 to the tissues and for waves reflecting back from the tissues to the ultrasound transducer 103; an underside region 113 is a surface area of the probe 101 located at the diametrically opposite side from the ultrasound transducer 103 on the probe 101; a tip 104 is the apex of the probe 101; a leading portion includes the tip 104, the transducer region 107 and the underside region 113 of the probe; and a longitudinal plane (see reference numeral 127 in FIG. 4) is an imaginary plane which cuts across the probe 101 longitudinally.

The sheath 105 includes a patch 106 affixed thereon by a liquid tight seal, thereby forming a liquid tight sack with an opening 109, a fluid introduction port, to receive the fluid introduction tube 111. The patch 106 is affixed to an area of the sheath 105 which corresponds in location to the transducer region 107 when the probe 101 is placed inside the sheath 105. The liquid tight seal between the patch 106 and the sheath 105 is achieved by gluing the patch 106 over the sheath 105. It should be noted, however, other similar methods of affixing the patch 106 onto the sheath 105, such as a heat treatment welding, solvent bonding, molding and adhesive bonding, are contemplated within the present invention. The patch 106 is, preferably, made of a more elastic material than that of the sheath. In an alternative embodiment, the elastic material of which the patch 106 is made can be identical to the material of which the sheath 105 is made. The sheath 105 is fastened to the probe 101 by a band 102. In alternative embodiments, other known method of fastening the sheath 105 to the probe 101 can be utilized, i.e., taping, strapping.

Figure 3:
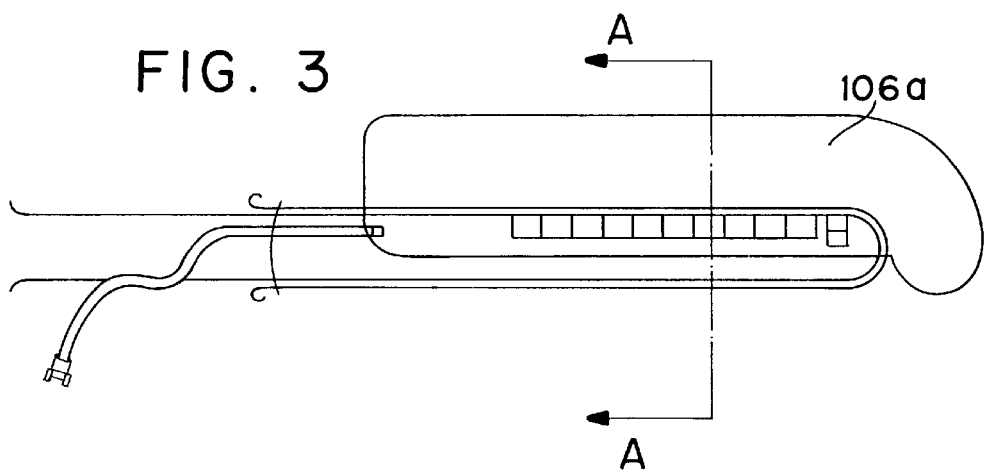
FIG. 3 is a side view of the probe with the sack expanded according to the first embodiment of the present invention.

The fluid introduction tube 111 is connected to a pump and a valve (not shown in the figures) such that liquid is introduced into or withdrawn from the sack. As the liquid is introduced into the sack, the patch 106a expands as illustrated in FIG. 3. Therefore, when the ultrasound transducer 103 is placed at a location to collect images of a tissue, the patch 106 can be expanded to form a liquid interface between the ultrasound transducer 103 and the tissue to be imaged. This liquid interface provides clear transmission paths for ultrasound waves emanating from the ultrasound transducer to the tissue to be imaged and for waves reflecting from the tissue back to the ultrasound transducer. The interface also places the transducer to be located at an adjustable distance from the tissue being imaged, thereby permitting the optimum focal length for the ultrasound transducer 103 to be achieved. These two goals in generating clear and undistorted images by the ultrasound transducer are achieved more readily using the present invention because the liquid introduced into the sack is not diverted into a circumferentially expanding the sack and filled into the underside 113 of the probe 101. It should be noted that the patch 106 preferably covers the transducer region 107 when the probe 101 is placed into the sheath, as discussed above. The patch 106, however, can also cover other areas outside of the transducer region 107 on the probe, as long as the goal of controlling the interface is not lost by including too much of other areas or by not covering the transducer region 107.

The seal between the sheath 105 and the patch 106 is preferably formed from the tip 104 of the probe 101 to the end of the of leading region along a longitudinal plane.

Figure 4:
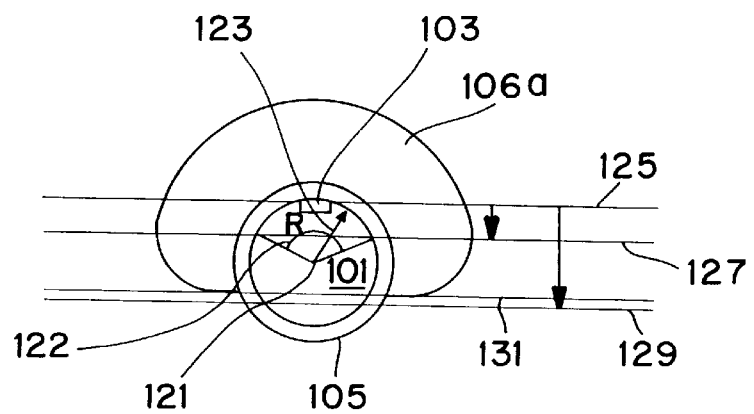
FIG. 4 is a magnified, frontal cross-sectional view of the probe and the expanded sack according to the first embodiment of the present invention.

More specifically, referring to FIG. 4, a radius of the probe 123 is defined as the distance from the center of the probe 121 to an outer surface of the probe, which is also designated as R, which is approximately 1 cm. A plurality of imaginary longitudinal planes are provided which runs the length of the probe 101. A top longitudinal plane 125 is a longitudinal plane tangential to the surface of the probe 101 where the ultrasound transducer 103 is located. Longitudinal planes designated with reference numerals 127 and 129 represent longitudinal planes located on the range of ⅖ R to ⅘ R from the top longitudinal plane 125. A longitudinal plane 131 that delineates the seal is located within this range. In other words, the location of the seal is defined, in part, by any longitudinal plane within the range of ⅖ R to ⅘ R from the top surface of the probe 101. Alternatively, the locations of the seal form an arc 122 viewed from the cross-sectional view of the probe as illustrated in FIG. 4. The arc 122 preferably has its angle on the range of 90°–200°. It should be understood that the locations of the seal are preferably completed in such a way that when the sack is expanded to form the interface, the interface covers the ultrasound transducer without causing distortion on the ultrasound waves emanating therefrom.

The seal, therefore, begins from the tip 104 of the probe where the tip and the longitudinal plane 131 cross each other, follows along the intersection between the longitudinal plane 131 and the outer surface of the probe, and encloses the sack at the other end of the leading portion (see reference numeral 108 in FIG. 2), thereby forming the liquid tight sack 106. It should be noted, however, the actual seal locations do not exactly have to match the intersection between the longitudinal plane 131 and the outer surface of the probe in order to provide a margin of error for manufacturing the sheaths.

Figure 5:
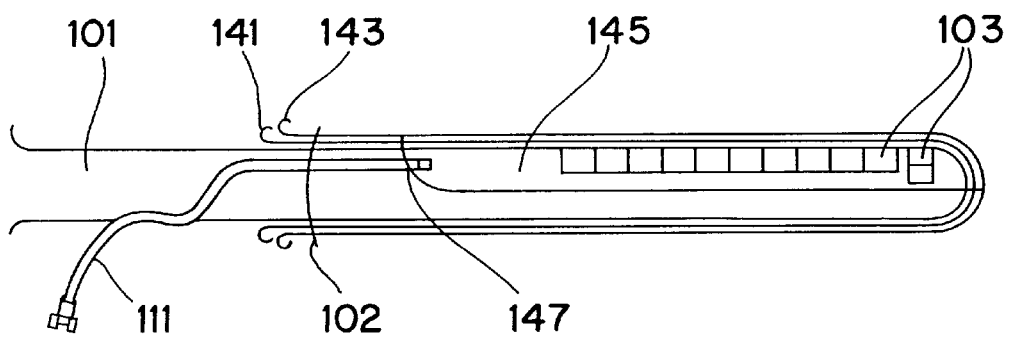
FIG. 5 is a side view of a probe with a sheath, which includes two layers, according to the second embodiment of the present invention.
Figure 6:
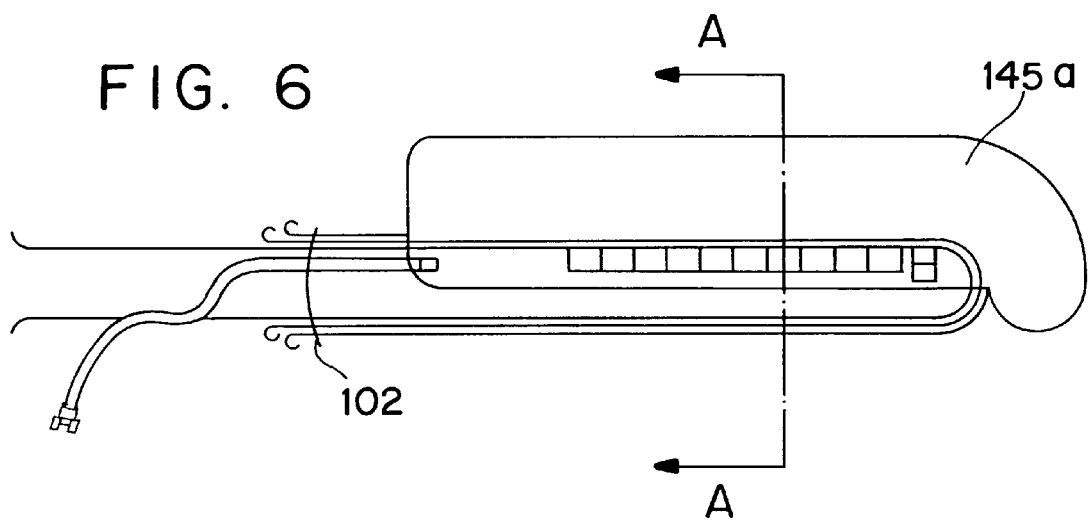
FIG. 6 is a side view of the probe with one of the layers of the sheath expanded according to the second embodiment of the present invention.
Figure 7:
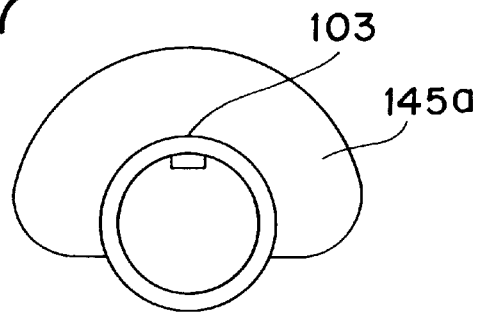
FIG. 7 is a frontal cross-sectional view of the probe and the expanded one of the layers of the sheath according to the second embodiment of the present invention.

Referring to FIG. 5, in a second embodiment of the present invention, a sheath is provided with two layers, a first and a second layers 141, 143. The first and second layers are affixed to each other to form a sack 145 as that of the first embodiment described above. In other words, by creating a sack 145 between the first and second layers 141, 143 of the sheath, a liquid can be introduced into the sack 145 via its fluid introduction port 147 by the fluid introduction tube 111 in order to expand the sack 145.

The seals between the two layers 141, 143 are created in the substantially same manner as that of the seal in the first embodiment. The second sheath layer 143, which expands, preferably is made of more elastic material than that of the first sheath layer 141. Also, it should be noted that the first and second layers 141, 143 can be made of same expandable material.

Figure 1:
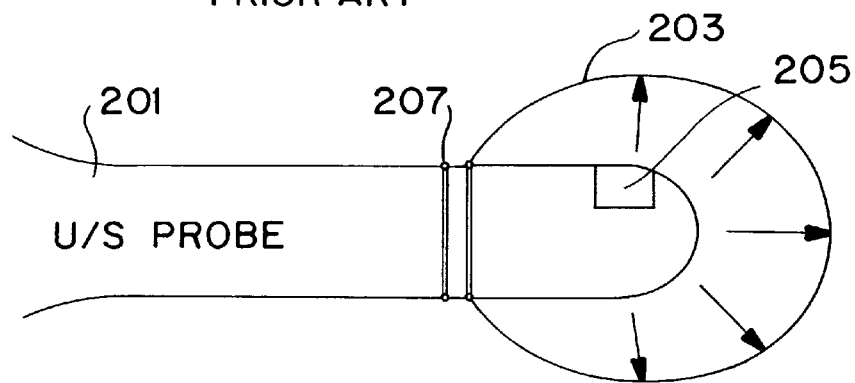
FIG. 1 is a side of view a probe with a conventional sheath.
Figure 8:
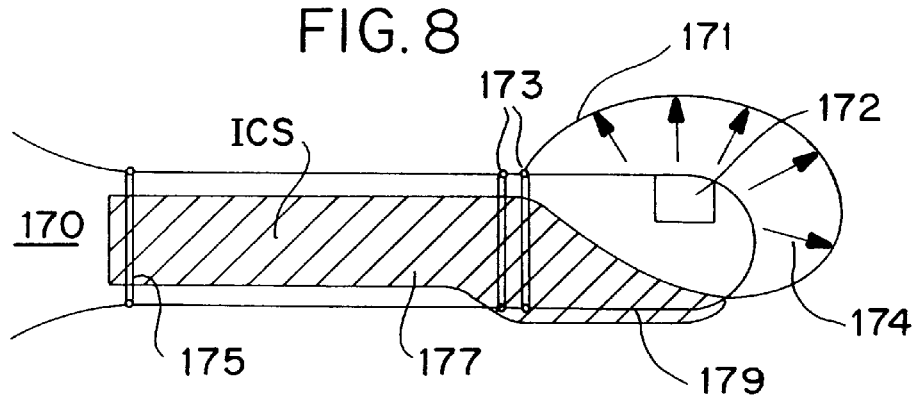
FIG. 8 is a side view of a probe with an interface control system (ICS) according to the third embodiment of the present invention.
Figure 9:
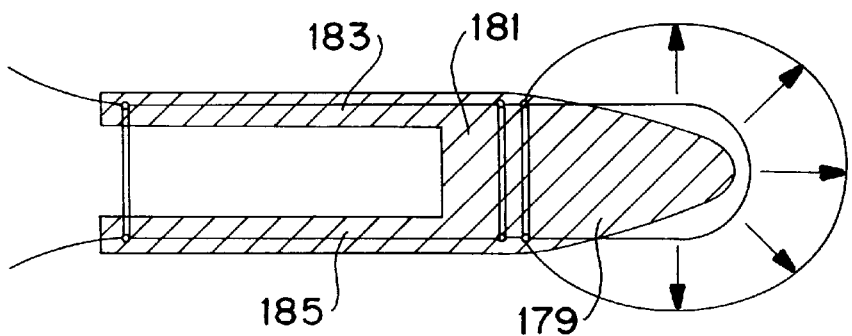
FIG. 9 is a bottom view of the probe with the ICS according to the third embodiment of the present invention.

Referring to FIGS. 8–9, a third preferred embodiment of the present invention includes a sheath 171, an ultrasound probe 170, placed inside the sheath 171, and an interface control system (ICS) 177, a splint which controls the direction to which the sheath 171 expands.

The probe 170 has a cylindrical body and includes an ultrasound transducer 172 which transmits and receives ultrasound waves for generating images of a tissue.

The sheath 171 in the third embodiment of this invention is a conventional sheath which is designed to fit snugly over the probe 170. The sheath is secured to the probe 170 by a plurality of bands 173 or o-rings to the probe, thereby forming a liquid tight area 174 into which a liquid can be introduced via a tube (not shown in FIGS. 8–9). In an alternative embodiment, no fluid introduction port is provided on the sack. In this alternative embodiment, the probe has a tube therein, which can be used to introduce the liquid into the sack. Unlike the conventional sheath, however, the sheath in this embodiment is prevented from expanding omni-directionally by the ICS 177.

The ICS 177 is made of a rigid material such as nylon, polyethylene, fiber reinforced plastic (or other composite material), polystyrene or the like. It should be noted, however, that any known rigid material that can prevent the sheath 171 from expanding and that can be used in medical examination is contemplated within this invention.

The ICS 177 includes a tongue-like portion 179, a body 181 which includes two arms 183, 185, and grooves 175 to receive at least one o-ring. The body 181 with its two arms 183, 185 are configured to fit snugly over the probe 170. When the ICS 177 is placed on the probe 170, the ICS 177 is fastened to the probe by a plurality of o-rings placed over the groove 175 in the ICS 177 and the probe 170. It should be noted, however, that other methods of fastening the ICS 177 on to the probe 170, such as designing the arms 183, 185 to snap on to the probe 170 or using bands in place of the o-rings, are contemplated within this invention. It should also be understood that the two arms 183, 185 are not an absolute requirement for the present invention. Instead, one continuous body, without the arms, can also be used in an alternative embodiment.

The tongue-like 179 portion, a cradling section, extends from the body 181 of the ICS 177 into the underside region of the leading portion of the probe 170. The tongue-like portion 179 not only prevents the sheath 171 from expanding omni-directionally but also helps controlling the direction in which the sheath 171 expands. In other words, when the ICS 177 is fastened to the probe 170, the sheath 171 is prevented from expanding from the underside region of the probe. This results in a controlled shape covering the ultrasound transducer, which provides a clear transmission path for ultrasound waves emanating from the ultrasound transducer to the tissue to be imaged and for ultrasound waves reflecting back from the tissue to ultrasound transducer. In other words, the shape of the tongue is configured in such a way that when the sheath is expanded to form the interface, the interface covers the ultrasound transducer without causing distortion on the ultrasound waves emanating therefrom.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A system for forming a liquid interface between body tissue and an ultrasound probe, the probe having top and bottom sides located diametrically opposite to each other viewed from a frontal cross-section of the probe and including an ultrasound transducer on the top side thereof, the system comprising:

a sheath configured and dimensioned to receive at least a portion of the probe, the sheath including a liquid tight expandable sack which covers the ultrasound transducer and a portion of the top side of the probe without covering the bottom side of the probe; and a tube operatively associated with the sack for directing a fluid into the sack for expansion thereof to form a liquid interface.

2. The system according to claim 1, further comprising a patch affixed to the sheath, wherein the patch and the sheath form the liquid tight sack.

3. The system according to claim 1, wherein the sheath includes first and second layers affixed to each other to form the liquid tight sack.

4. The system according to claim 1, further comprising:
a fastener to secure the sheath to the probe and to form the liquid tight sack between the sheath and the probe; and
a splint made of a rigid material configured to restrict the sheath from expanding from the bottom side of the probe.

5. The system according to claim 4, wherein the fastener includes at least one o-ring.

6. The system according to claim 4, wherein the splint is a separate component that is positioned over a portion of the sheath and is fastened to the probe.

7. The system according to claim 4, wherein the splint is integrally formed with the sheath.

8. The system according to claim 1, wherein the area covered by the sack on the probe is substantially delineated in part by an intersection between an imaginary longitudinal plane and the surface of the probe, wherein the longitudinal plane is located between $2/5$ and $8/5$ of the radius of the probe from the top side of the probe.

9. The system according to claim 1, wherein the sheath further comprising a fluid introduction port configured to be connected to the fluid introduction tube.

10. A system for forming a liquid interface between body tissue and an ultrasound probe, the probe having top and bottom sides located diametrically opposite to each other viewed from a frontal cross-section of the probe and including an ultrasound transducer on the top side thereof, the system comprising:
a sheath having a liquid tight sack which is configured and dimensioned to cover the ultrasound transducer and a portion of the top side of the probe when the probe is placed inside the sheath, without covering the bottom side of the probe; and
a fluid introduction port configured to receive a tube for introducing liquid into the sack, wherein the sack expands when receiving liquid to form the liquid interface.

11. The system according to claim 10, further comprising a patch affixed to the sheath, wherein the patch and the sheath form the liquid tight sack.

12. The system according to claim 10, wherein the sheath includes first and second layers affixed to each other to form the liquid tight sack.

13. The system according to claim 10, further comprising:
a fastener to secure the sheath to the probe and to form the liquid tight sack between the sheath and the probe; and
a splint made of a rigid material configured to restrict the sheath from expanding from the underside of the probe.

14. The system according to claim 13, wherein the fastener includes at least one o-ring.

15. The system according to claim 13, wherein the splint is formed on the sheath.

16. The system according to claim 13, wherein the splint is fastened to the probe.

17. The system according to claim 10, wherein the area covered by the sack on the probe is substantially delineated in part by an intersection between an imaginary longitudinal plane and the surface of the probe, wherein the longitudinal plane is located between from $2/5$ and $8/5$ of the radius of the probe from a surface of the probe where the ultrasound transducer is located.

18. A system for forming a liquid interface between body tissue and an ultrasound probe, the probe having top and bottom sides located diametrically opposite to each other viewed from a frontal cross-section of the probe and including an ultrasound transducer on the top side thereof, the system comprising:
a sheath covering at least a portion of the ultrasonic probe and having a fluid introduction port for introducing fluid into the sheath to expand the sheath, an ultrasonic probe tip insertable into a body cavity, and at least one transducer located on the probe tip for imaging body tissue; and
a splint comprising:
a body section configured and dimensioned to fit around a portion of the ultrasonic probe;
a cradling section extending from the body section and substantially covering a region of the ultrasonic probe tip opposite the transducer; and
at least one fastening element for securing the splint to the ultrasonic probe,
wherein the splint is made of a material having sufficient rigidity to substantially prevent the sheath from expanding in the region covered by the cradling section.

* * * * *